United States Patent

Stock

[11] Patent Number: 6,075,246
[45] Date of Patent: Jun. 13, 2000

[54] INFRARED MEASURING ARRANGEMENT WITH EXPANDED MEASURING RANGE

[75] Inventor: Burkhard Stock, Lübeck, Germany

[73] Assignee: Dräger Sicherheitstechnik GmbH, Germany

[21] Appl. No.: 09/019,234

[22] Filed: Feb. 5, 1998

[30] Foreign Application Priority Data

Sep. 24, 1997 [DE] Germany ............... 197 42 053

[51] Int. Cl.[7] .................................................. G01N 21/61
[52] U.S. Cl. .......................................................... 250/343
[58] Field of Search ............................. 250/343, 340, 250/353, 373; 356/437, 439

[56] References Cited

U.S. PATENT DOCUMENTS

| | | |
|---|---|---|
| 3,761,724 | 9/1973 | Dennis . |
| 5,222,389 | 6/1993 | Wong ........................ 73/31.02 |
| 5,874,737 | 2/1999 | Bytyn et al. ................ 250/343 |
| 5,908,789 | 6/1999 | Weckstrom ................. 436/133 |

FOREIGN PATENT DOCUMENTS

| | | |
|---|---|---|
| 2211835 | 8/1973 | Germany . |
| 28 16 541 C2 | 10/1978 | Germany . |
| 35 09 532 C2 | 9/1986 | Germany . |
| 195 28 919 A1 | 2/1997 | Germany . |
| 394853 | 7/1933 | United Kingdom . |
| WO 96/01418 | 1/1996 | WIPO . |

*Primary Examiner*—Constantine Hannaher
*Assistant Examiner*—Albert Gagliardi

[57] ABSTRACT

An infrared measuring arrangement with essentially expanded measuring range with an infrared radiation source (3) and an infrared radiation detector (4). The infrared radiation source (3) has a first, direct beam path to the infrared radiation detector (4), on the one hand, and, on the other hand, a second, reflected beam path to the infrared radiation detector (4), which is longer than the first one.

21 Claims, 2 Drawing Sheets

INFRARED MEASURING ARRANGEMENT WITH EXPANDED MEASURING RANGE

FIELD OF THE INVENTION

The present invention pertains to an arrangement for measuring infrared absorption with an infrared radiation source and an infrared radiation detector.

BACKGROUND OF THE INVENTION

A measuring arrangement of this type for the nondispersive measurement of the infrared absorption with a fixed absorption measuring section has been known from, e.g., DE 3509532 C2.

In such nondispersive infrared measuring arrangements, the attenuation of the infrared radiation absorbed by the gas to be determined after passing through a predetermined absorption section is an indicator of the gas concentration present.

The relationship between the intensity I at the end of the absorption section and the gas concentration C is described by the Bouguer-Lambert-Beer law:

$$I(C) = I_0 \cdot \exp(-e \cdot L \cdot C)$$

in which $I_0$=intensity at entry; e=extinction coefficient;
L=absorption section; C=gas concentration.

It is important for the high sensitivity of the instruments that a sufficient amount of infrared radiation shall reach the infrared radiation detector in order for the detector noise not to become too intense, and that the measured intensity I(C) shall change as greatly as possible if the concentration C is changing.

It is seen from the equation given above that due to being in the exponent, only little infrared radiation reaches the infrared radiation detector at high concentrations, and the change in the signal as a function of the change in the gas concentration is weak as well.

Consequently, to achieve high sensitivity, the sensitivity of the absorption section L must be adapted to the concentration to be measured, i.e., short sections shall be used for high concentrations and vice versa. Consequently, if the concentration range to be measured varies within a broad range, two sample holders with absorption sections of different lengths are actually needed.

SUMMARY AND OBJECTS OF THE INVENTION

The object of the present invention is to provide an arrangement for measuring the infrared absorption, with which an expanded measuring range can be covered.

According to the invention, an arrangement for measuring the infrared absorption with an infrared radiation source and an infrared radiation detector is provided. The infrared radiation source has, on the one hand, a first, direct beam path to the infrared radiation detector and, on the other hand, a second, reflected beam path to the infrared radiation detector. The second beam path is longer than the first beam path.

The arrangement may be built into a tubular, internally metallized measuring gas sample holder. The infrared radiator detector is preferably arranged at one of the two narrow sides and the infrared radiation source may be arranged at a long side of the said measuring gas sample holder.

The infrared radiation source may be arranged in the focal point of the said mirror or in the vicinity of the focal point.

The infrared radiation detector may be arranged at a greater distance from the mirror than the infrared radiation source, wherein the infrared radiation detector receives both the radiation of the infrared radiation source reflected from the mirror and the non-reflected radiation of the. infrared radiation source.

The light intensity of the infrared radiation source may be split by means of diaphragms between the two beam paths, preferably at an intensity ratio of 1:1.

The last 3 to 6 mm of the inner surface of the tubular measuring gas sample holder may be dereflected.

One essential advantage of the present invention is that a broad measuring range of different gas concentrations can be measured with a single arrangement at a good measuring sensitivity.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
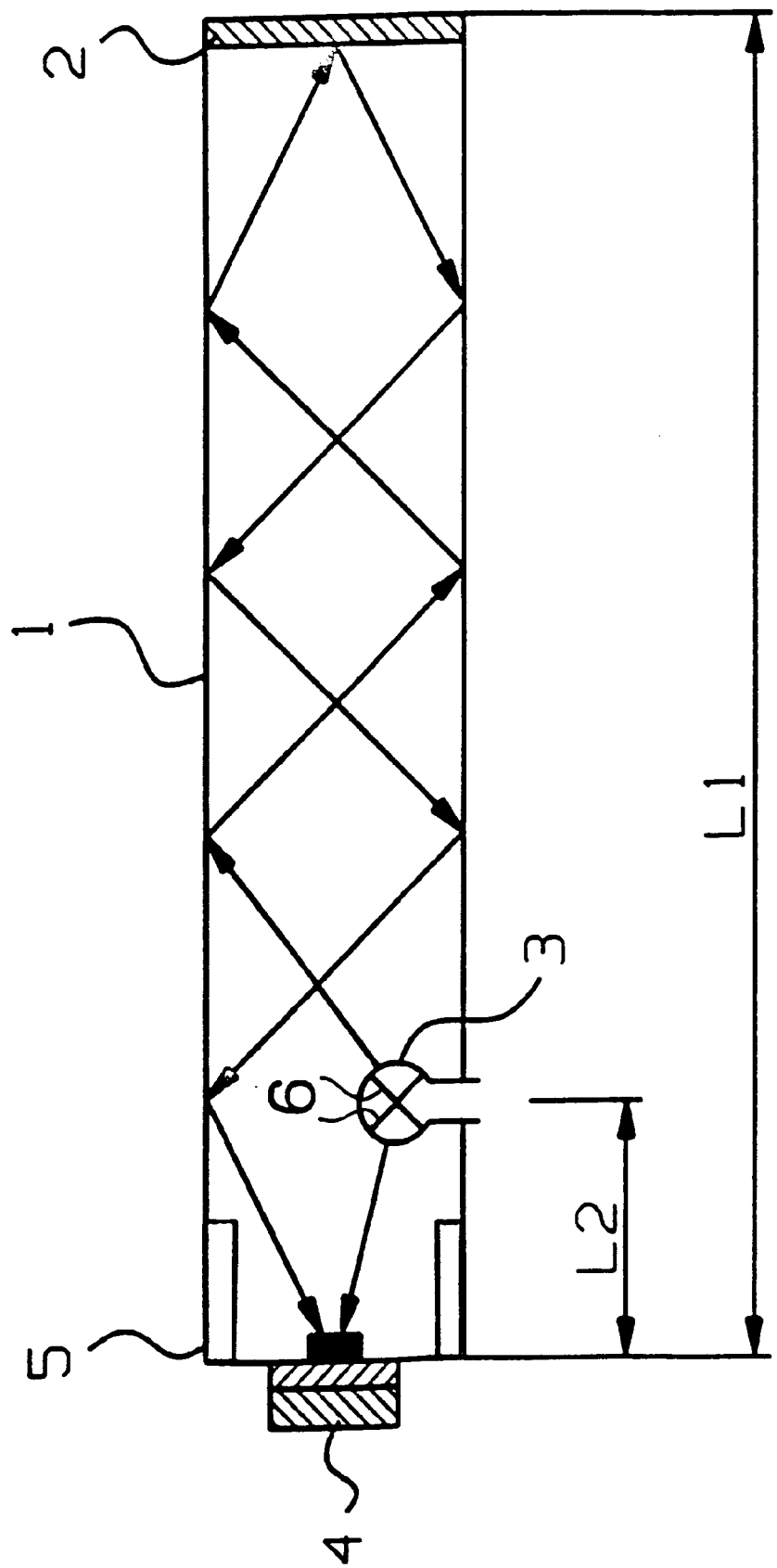
FIG. 1 is a first exemplary embodiment of the present invention.

Referring to the drawings in particular, the exemplary embodiment according to FIG. 1 shows an arrangement according to the present invention in the form of a single, cylindrical or tubular measuring gas sample holder 1. Contrary to the example in FIG. 2, this is a non-imaging system. The measuring gas sample holder 1 comprises essentially an internally metallized, closed tube with a gas inlet, not shown. This tube is closed with a likewise metallized surface, e.g., with a plane mirror 2, at the end that is the right-hand end in FIG. 1. The infrared radiation source 3, typically a suitable incandescent lamp, is located at a distance of about 1 to 2 cm from the infrared radiation detector 4. The infrared radiation emitted in the forward direction, i.e., to the left in FIG. 1, falls directly on the infrared radiation detector 4 with corresponding filters, and the infrared radiation emitted to the rear, i.e., to the right in FIG. 1, reaches the end of the tube, is reflected several times, returns, and then falls on the infrared radiation detector 4 with corresponding filters, this second beam path being, of course, substantially longer than the first one. The splitting of the infrared radiation between the two different beam paths is best performed via diaphragms 6, preferably at a 1:1 split to the two beam paths.

In the case of such an equal splitting of the infrared radiation between two beam paths, the arrangement can be described in a simplified manner as follows as a parallel connection of two sample holders with different absorption sections $L_A$ and $L_B$ concerning the concentration-dependent intensity:

$$I(C) = \tfrac{1}{2} \cdot (I_0 \cdot \exp(-e \cdot L_A \cdot C) + I_0 \cdot \exp(-e \cdot L_B \cdot C)).$$

It was confirmed by measurements that, on the one hand, an expansion of the measuring range is achieved by the splitting of the radiation according to the present invention, i.e., the change in the intensity signal as a function of a change in concentration is improved, i.e., increased.

The dimensioning of the optical arrangement according to the present invention depends on the required measuring range. The distance between the infrared radiation detector 4 and the plane mirror 2 ($L_1$ in FIG. 1), i.e., half the longer absorption section, is determined by the lower limit of the concentration to be measured, because great absorption lengths are needed for low concentrations: According to a typical example, namely, the measurement of the $CO_2$ concentration, an absorption section of 0.5 to 1 cm is optimal for concentrations in the range of 30 to 100 vol. %, whereas an absorption section of 20 cm is very suitable for the measurement of concentrations in the range of up to 100 ppm.

The diameter of the plane mirror 2 is obtained from the required signal-to-noise ratio. The larger the diameter, the more infrared radiation falls on the infrared radiation detector 4. However, the diameter must be brought into relation to the length ($L_1$) of the tube in order for the angle at which the light arrives from the peripheral areas of the plane mirror 2 not to fall too obliquely on the infrared radiation detector 4. Most of it is otherwise reflected by the interference filter or filters, not shown, before the infrared radiation detector 4, and it also causes a shift in the central wavelength of these filters.

In a typical example, the tube length ($L_1$) is preferably about 100 to 200 mm, the length $L_2$ is about 10 to 20 mm, and the tube diameter is likewise about 10 to 15 mm. If the diameter becomes too small, the size of the infrared radiation source 3 becomes a disturbance. If the diameter becomes too large, the intensity of light at the face of the detector becomes too weak because of the larger area. A ring-shaped inner surface 5 of the measuring gas sample holder 1 is preferably dereflected over about the last 3 to 6 mm of the tube. This is advantageous for blanking out peripheral rays, which fall on the infrared radiation detector 4 at a very steep angle and may compromise the measured result. The longer absorption section, i.e., the longer beam path, is about $2 \cdot L_1$, the direct beam path $L_2$, due to the reflection at the plane mirror 2.

Figure 2:
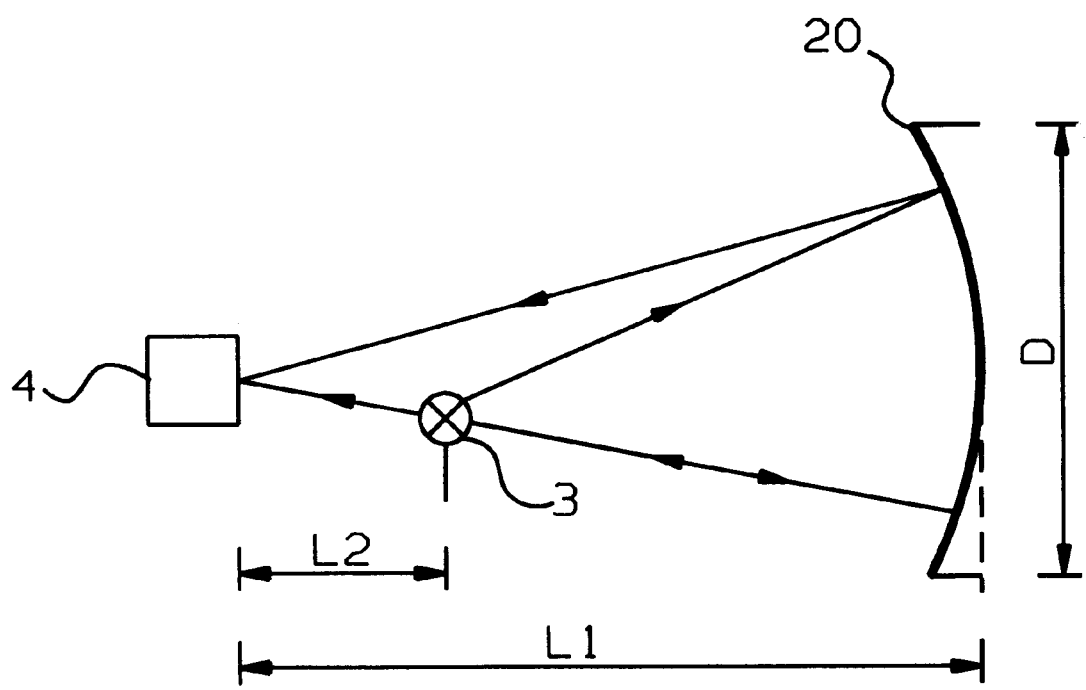
FIG. 2 is a second exemplary embodiment of the present invention.

FIG. 2 shows an arrangement according to the present invention with a mirror 20 provided with a reflecting coating, preferably a concave mirror, and likewise with an infrared radiation source 3 and an infrared radiation detector 4 with corresponding filters, preferably arranged in the focal point of the infrared radiation source 3. This arrangement may be arranged in or introduced into either a sample holder containing gas to be measured, not shown, or an environment enriched with gas to be measured e.g., as a portable or mobile measuring arrangement. The diameter D of the mirror 20 should not be greater than the section $L_1$, the mirror 20 reflecting the total amount of infrared radiation of the longer beam path emitted by the infrared radiation source 3 to the infrared radiation detector 4. If the diameter D is selected to be too large in relation to $L_1$, the reflected infrared radiation falls on the infrared radiation detector 4 too obliquely and, on the whole, it compromises the measured signal.

The distance between the infrared radiation detector 4 and the infrared radiation source 3 (section $L_2$ in FIG. 1 and FIG. 2) is determined by the upper measuring range of the gas concentration to be measured. The measurement of very high gas concentrations requires a very small $L_2$ on the order of magnitude of the diameter of the infrared radiation source 3. In this case, the infrared radiation source 3 must be offset from the optical axis for the embodiment according to FIG. 2, because it would otherwise cover the light reflected by the mirror 20. However, $L_2 = \frac{1}{2} L_1$ is usually selected in order to obtain a constant quality of measurement over the entire measuring range of the concentrations to be determined. The quality of measurement is otherwise poor in the middle range at extreme ratios, e.g., in the case of $L_2 = 0.1 \cdot L_1$, because the lower and upper measuring ranges will no longer overlap.

Once $L_1$ and $L_2$ have been selected, the focal distance of the mirror 20 can be set based on the desired condition that the image of the infrared radiation source 3 appear on the infrared radiation detector 4. In the practical example for $CO_2$ measurement, $L_2$ equals about 20 mm, $L_1$ about 50 to 100 mm, and the diameter D of the mirror 20 is about 30 mm.

While specific embodiments of the invention have been shown and described in detail to illustrate the application of the principles of the invention, it will be understood that the invention may be embodied otherwise without departing from such principles.

What is claimed is:

1. An arrangement for measuring the infrared absorption in a gas sample, the arrangement comprising:
   an infrared radiation source;
   an infrared radiation detector having a sensitivity range;
   a first substantially direct infrared radiation source beam path to said infrared radiation detector, said first beam path having a first beam length in the gas sample to have said sensitivity range to measure gas concentrations within a first portion of a measuring range; and,
   a second, reflected infrared radiation source beam path to said infrared radiation detector, said second beam path being longer than the first beam path, said second beam path having a second beam length in the sample to have said sensitivity range measure the gas concentrations within a second portion of the measuring range.

2. The arrangement in accordance with claim 1, further comprising:
   a tubular, internally metallized measuring gas sample holder, wherein said infrared radiation detector is arranged at one of two narrow sides and said infrared radiation source is arranged at a long side of said measuring gas sample holder;
   a mirror arranged at another one of said two narrow sides of said measuring gas sample holder.

3. The arrangement in accordance with claim 1, further comprising:
   a mirror positioned in said second beam path, said infrared radiation source is arranged in a focal point of said mirror or in the vicinity of the focal point, and said infrared radiation detector is arranged at a greater distance from said mirror than said infrared radiation source, wherein said infrared radiation detector receives both the radiation of said infrared radiation source reflected from said mirror and the non-reflected radiation of said infrared radiation source.

4. The arrangement in accordance with claim 1, wherein light intensity of said infrared radiation source is split by means of diaphragms between said first and second beam paths.

5. The arrangement in accordance with claim 4, wherein a last 3 to 6 mm of an inner surface of said tubular measuring gas sample holder is dereflected.

6. The arrangement in accordance with claim 1, wherein a last 3 to 6 mm of an inner surface of said tubular measuring gas sample holder is dereflected.

7. The arrangement in accordance with claim 1, wherein:
light intensity of said infrared radiation source is split by means of diaphragms between said first and second beam paths at an intensity ratio of substantially 1:1.

8. The arrangement in accordance with claim 1, further comprising:
a tubular gas sample holder having first and second ends, said infrared radiation detector is arranged at said first end, and said infrared radiation source is between said first and second ends;
a mirror arranged at said second end, said radiation source being closer to said radiation detector than to said mirror.

9. The arrangement in accordance with claim 8, wherein:
said first beam path extends directly from said radiation source to said radiation detector;
said second beam path extends from said radiation source to said mirror and from said mirror to said radiation detector.

10. An arrangement for measuring gas concentrations in a gas sample within a measuring range, the arrangement comprising:
an infrared radiation source;
an infrared radiation detector having a sensitivity range;
a first beam path from said infrared radiation source to said infrared radiation detector, said first beam path having a first beam length in the gas sample having said sensitivity range to measure gas concentrations within a first portion of the measuring range;
a second beam path from said infrared radiation source to said infrared radiation detector, said second beam path having a second beam length in the sample to have said sensitivity range measure the gas concentrations within a second portion of the measuring range.

11. The arrangement in accordance with claim 10, wherein:
said second beam length includes a mirror with said second beam path reflecting off said mirror, said second beam length being longer than said first beam length;
said infrared radiation source is closer to said infrared radiation detector than to said mirror.

12. The arrangement in accordance with claim 11, further comprising:
a tubular gas sample holder holding the gas sample and having first and second ends, said infrared radiation detector is arranged at said first end, and said infrared radiation source is arranged on a circumferential side of said sample holder between said first and second ends, said mirror being arranged at said second end.

13. The arrangement in accordance with claim 11, wherein:
said first beam path extends directly from said infrared radiation source to said infrared radiation detector;
said mirror is concave.

14. The arrangement in accordance with claim 11, wherein:
said mirror is concave and focuses infrared radiation from said infrared radiation source to said infrared radiation detector.

15. The arrangement in accordance with claim 14, wherein:
said infrared radiation detector is positioned at a focal point of said mirror.

16. The arrangement in accordance with claim 10, wherein:
said second beam length is substantially twice as long as said first beam length.

17. The arrangement in accordance with claim 10, wherein:
said first beam length corresponds to an upper end of the measuring range;
said second beam length corresponds to a lower end of the measuring range.

18. The arrangement in accordance with claim 10, wherein:
each of said first and second portions are less than the measuring range.

19. The arrangement in accordance with claim 10, wherein:
said first and second portions of the measuring ranges are adjacent with minimum overlap.

20. The arrangement in accordance with claim 19, wherein:
a size of said overlap is less than a size of said first portion of the measuring range not in said overlap.

21. The arrangement in accordance with claim 10, wherein:
said first and second beam lengths are chosen to have said first and second portions of the measuring range be adjacent and to maximize a sum of said first and second portions.

* * * * *